(12) United States Patent
Satoh

(10) Patent No.: US 7,393,324 B2
(45) Date of Patent: Jul. 1, 2008

(54) ULTRASONIC TRANSMITTING AND RECEIVING APPARATUS

(75) Inventor: Tomoo Satoh, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 152 days.

(21) Appl. No.: 11/175,168

(22) Filed: Jul. 7, 2005

(65) Prior Publication Data

US 2006/0036169 A1 Feb. 16, 2006

(30) Foreign Application Priority Data

Jul. 13, 2004 (JP) ............................. 2004-205706

(51) Int. Cl.
*A61B 8/00* (2006.01)

(52) U.S. Cl. ..................................... 600/437

(58) Field of Classification Search ................ 600/443, 600/447, 454–456, 458, 437, 459; 128/660; 356/5.03

See application file for complete search history.

(56) References Cited

U.S. PATENT DOCUMENTS 5,835,199 A * 11/1998 Phillips et al. ............. 356/5.03
7,066,886 B2 * 6/2006 Song et al. ................. 600/443
2002/0128555 A1 * 9/2002 Maxwell et al. ............ 600/447

FOREIGN PATENT DOCUMENTS

JP 7-104063 A 4/1995
WO WO 97/36188 A1 10/1997

* cited by examiner

*Primary Examiner*—Eric F. Winakur
*Assistant Examiner*—Lawrence N Laryea
(74) *Attorney, Agent, or Firm*—Sughrue Mion, PLLC

(57) ABSTRACT

An ultrasonic transmitting and receiving apparatus in which scanning time is shortened by simultaneously transmitting plural ultrasonic beams in plural directions and separation among the plural ultrasonic beams is improved. The ultrasonic transmitting and receiving apparatus includes: an ultrasonic probe including plural ultrasonic transducers; a drive signal generating unit for generating plural drive signals for simultaneously transmitting in plural directions plural kinds of ultrasonic beams corresponding to plural kinds of spread spectrum signals obtained by adding at a predetermined rate frequency components which have been discretely selected from among plural frequency components having different center frequencies; and a reception side signal processing unit for performing plural kinds of phase matching so as to form plural reception focal points corresponding to a number of transmitted ultrasonic beams based on plural reception signals.

8 Claims, 6 Drawing Sheets

FIG.6
*PRIOR ART*
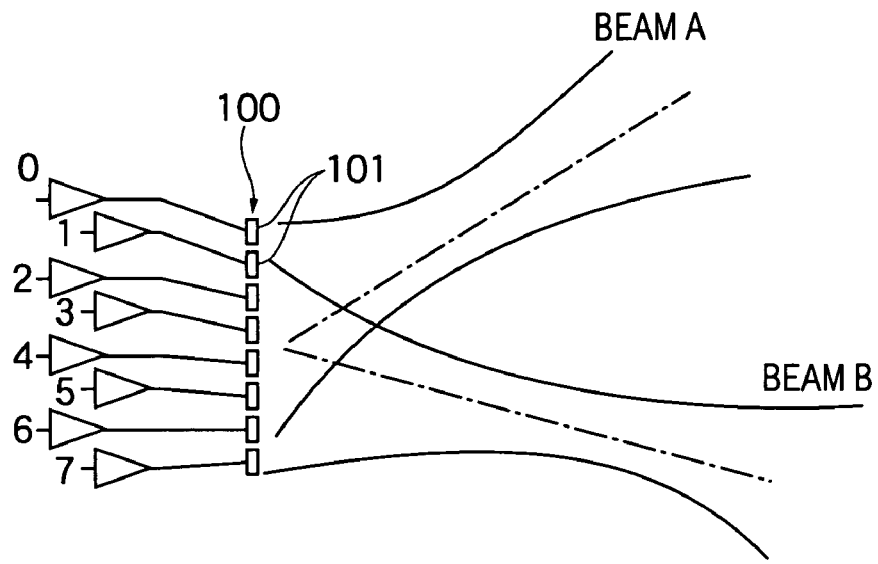
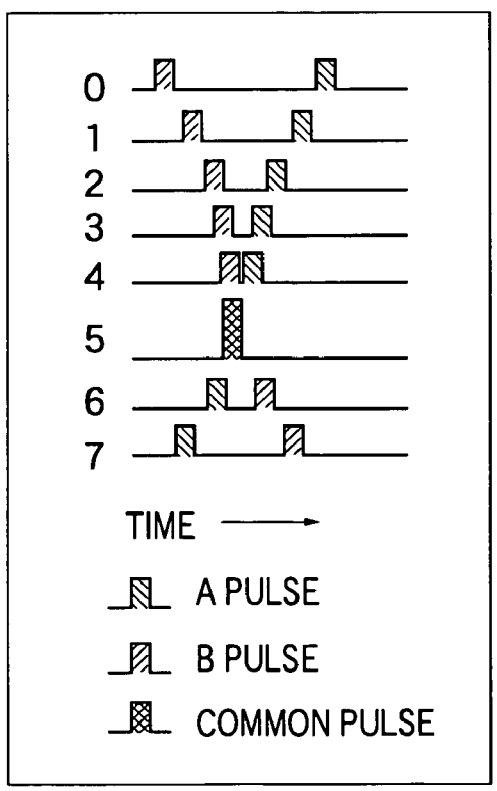

ULTRASONIC TRANSMITTING AND RECEIVING APPARATUS

BACKGROUND OF THE INVENTION

1. Field of the Invention

The present invention relates to an ultrasonic transmitting and receiving apparatus to be used for diagnoses of organs in a living body and nondestructive inspections by transmitting and receiving ultrasonic waves.

2. Description of a Related Art

Generally, in an ultrasonic transmitting and receiving apparatus to be used as an ultrasonic diagnostic apparatus and an industrial flaw detecting apparatus, etc., an ultrasonic probe is used which includes plural ultrasonic transducers having functions of transmitting and receiving ultrasonic waves. Image information on an object to be inspected is obtained based on intensity of ultrasonic echoes by scanning the object with an ultrasonic beam formed by combining plural ultrasonic waves and receiving ultrasonic echoes reflected from inside of the object by using such an ultrasonic probe. Further, a two-dimensional or three-dimensional image on the object is reproduced based on the image information.

In the ultrasonic transmitting and receiving apparatus, as a method of transmitting and receiving an ultrasonic beam by using an ultrasonic transducer array formed by plural ultrasonic transducers, the following methods (1) and (2) are known.

(1) Method of Dividing Beams on Reception

FIG. 5A is a schematic diagram for explanation of transmitting an ultrasonic beam according to a conventional method, and FIG. 5B is a schematic diagram for explanation of receiving an ultrasonic beam according to the conventional method. In this method, ultrasonic pulses are intermittently transmitted from respective plural ultrasonic transducers 101 that form an ultrasonic transducer array 100 based on drive signals supplied from plural pulsers provided in a transmission system. Those ultrasonic pulses are transmitted from the ultrasonic transducer array 100 toward an object to be inspected as shown in FIG. 5A, and propagates within the object to form an ultrasonic beam 102.

The ultrasonic beam 102 gradually becomes narrower while it travels in a region at a short distance from the beam transmitting position, becomes narrowest at a focal point F, and gradually becomes broader afterwards. The ultrasonic beam is reflected by a reflector existing within the object so that an ultrasonic echo is generated. As shown in FIG. 5B, the ultrasonic echo is received by the ultrasonic transducer array 100. The plural ultrasonic transducers 101, which form the ultrasonic transducer array 100, output RF signals. Predetermined delays are given to the RF signals and the RF signals are added to each other. Thus the RF signals are subjected to reception beam forming processing by phase matching computing means provided in a reception system, and thereby, reception signals with respect to each ultrasonic beam are obtained. In this example, three reception ultrasonic beams 103, 104, and 105 are shown.

(2) Method of Simultaneously Transmitting Multidirectional Beams

FIG. 6 is a schematic diagram for explanation of transmission and reception of ultrasonic beams according to another conventional method. In this method, plural kinds of drive signals are simultaneously supplied from plural pulsers to ultrasonic transducers 101. For example, as shown in FIG. 6, two sets of timing pulses including "A" pulse and "B" pulse are applied to one set of elements so that an ultrasonic beam "A" and an ultrasonic beam "B" are generated. In the case where the "A" pulse and the "B" pulse overlap, they form a common pulse. Thus, plural ultrasonic beams are simultaneously transmitted in plural directions (two directions in FIG. 6).

When the ultrasonic beams are received, reception beam forming processing is performed on the RF signals outputted from the ultrasonic transducers 101 in accordance with the directions in which the ultrasonic beam "A" and the ultrasonic beam "B" have been transmitted, and thereby, the two ultrasonic beams are separated. However, since sufficient separation cannot be obtained in the case where the angular difference between the transmitted ultrasonic beam "A" and ultrasonic beam "B" is small, a scheme is required for distinguishing these ultrasonic beams.

As a related technology, Japanese Patent Application Publication JP-A-7-104063 discloses an ultrasonic object measurement apparatus having a relatively simple construction and capable of precisely measuring existence or nonexistence of an object and the distance by reducing (i) influence of surrounding ultrasonic noise and (ii) influences of occurrence of mutual interference and multiple reflection waves when plural ultrasonic converters are operated close to each other in parallel (page 1, FIG. 1). This ultrasonic object measurement apparatus performs spread frequency modulation on a tone burst wave by using a pseudo-noise signal and transmit the wave, and obtains cross-correlation between the signal generated by receiving and demodulating the reflection wave and the pseudo-noise signal used for the spread frequency modulation. The existence or nonexistence of reception of reflection signal from the object is determined according to a degree of the cross-correlation, and further, the distance is measured. Furthermore, plural tone burst waves are distinguished by sending out transmission tone burst wave by using spread frequency modulation signals distinguished by sequential switching among plural pseudo-noise signals.

JP-A-7-104063 discloses that plural M-sequences (maximal-length sequences) codes having different periods from each other are used as plural pseudo-noise signals. However, there is a problem that the crosstalk among the plural tone burst waves, which are respectively modulated by using the plural M-sequences codes, does not become smaller than a certain fixed value in the worst case.

Further, International Publication WO97/36188 discloses an ultra-wideband interference radar system for optimization of radio interference discrimination ability and evaluation of Doppler shift of reflection radar echo. In this radar system, the transmission and reception process is divided into multiple and continuous sub-processes, and each sub-process includes transmission and reception of a signal having a relative bandwidth of a part of one octave, subsequent thereto. The signals received by different narrow-band transmissions are used for reconstruction of wideband radar data in accordance with the pulse compression technology. However, there is a problem that time is required for data collection because the transmission and reception process is divided into multiple and continuous subprocesses.

SUMMARY OF THE INVENTION

The present invention has been achieved in view of the above-described problems. An object of the present invention is to provide an ultrasonic transmitting and receiving apparatus in which the time required for scanning an object to be inspected is shortened by simultaneously transmitting plural ultrasonic beams in plural directions and separation among the plural ultrasonic beams is improved.

In order to solve the above-described problems, an ultrasonic transmitting and receiving apparatus according to the present invention comprises: an ultrasonic probe including plural ultrasonic transducers for transmitting ultrasonic waves to an object to be inspected according to plural drive signals and receiving ultrasonic echoes reflected from the object to output plural reception signals, respectively; drive signal generating means for generating plural drive signals for simultaneously transmitting from the ultrasonic probe in plural directions plural kinds of ultrasonic beams corresponding to plural kinds of spread spectrum signals obtained by adding frequency components, which have been discretely selected from among plural frequency components having different center frequencies in a transmission band, to each other at a predetermined rate; and reception side signal processing means for performing signal processing on the plural reception signals respectively outputted from the plural ultrasonic transducers and performing plural kinds of phase matching so as to form plural reception focal points corresponding to a number of ultrasonic beams transmitted from the ultrasonic probe based on the plural reception signals which have been subjected to the signal processing.

According to the present invention, plural ultrasonic beams are simultaneously transmitted in plural directions based on plural kinds of spread spectrum signals obtained by adding plural frequency components, which have been discretely selected from among plural frequency components having different center frequencies in a transmission band, at a predetermined rate, and thereby, the time required for scanning the object can be shortened and the separation among ultrasonic beams can be improved.

Note that, in the application, a transducer for one element that forms a transducer array is referred to as "ultrasonic transducer".

BRIEF DESCRIPTION OF THE DRAWINGS

FIG. 6 is a schematic diagram for explanation of transmission and reception of ultrasonic beams according to another conventional method.

DESCRIPTION OF THE PREFERRED EMBODIMENTS

Figure 1:
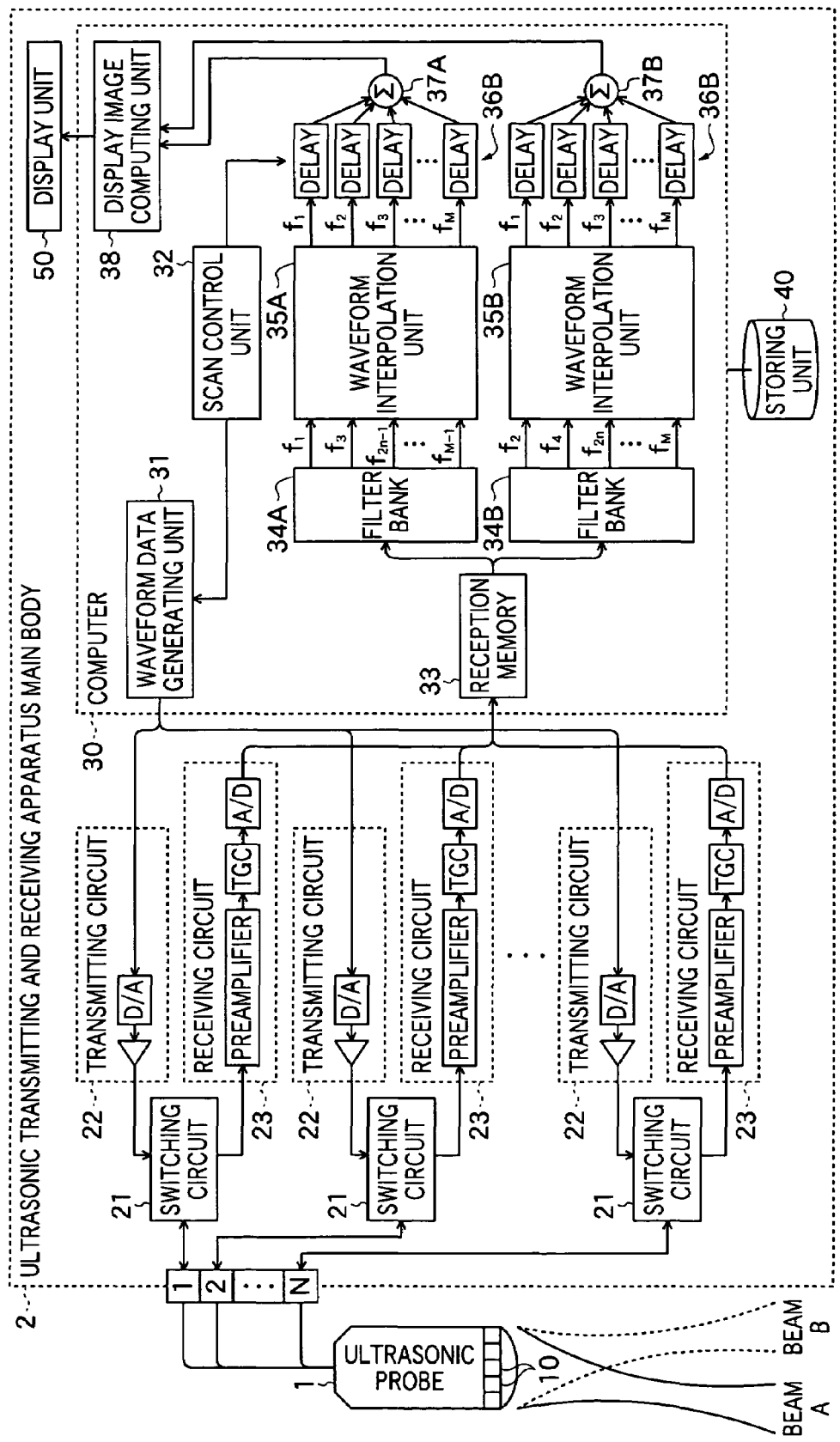
FIG. 1 is a block diagram showing a constitution of an ultrasonic transmitting and receiving apparatus according to one embodiment of the present invention.

Hereinafter, a preferred embodiment of the present invention will be described in detail by referring to the drawings. The same reference numbers will be assigned to the same component elements and the description thereof will be omitted.

FIG. 1 is a block diagram showing a constitution of an ultrasonic transmitting and receiving apparatus according to one embodiment of the present invention. The ultrasonic transmitting and receiving apparatus according to the embodiment has functions of transmitting ultrasonic waves toward an object to be inspected and receiving ultrasonic echoes reflected from the object to display ultrasonic images based on the received ultrasonic echoes.

As shown in FIG. 1, the ultrasonic imaging apparatus includes an ultrasonic probe 1 to be used in abutment contact with the object, and an ultrasonic transmitting and receiving apparatus main body 2 connected to the ultrasonic probe 1.

The ultrasonic probe 1 incorporates an ultrasonic transducer array (also referred to as "array transducer") including N ultrasonic transducers 10 arranged in a one-dimensional or two-dimensional manner. These ultrasonic transducers 10 are connected to the ultrasonic transmitting and receiving apparatus main body 2 via signal lines.

The ultrasonic transducers 10 includes a vibrator in which electrodes are formed on both ends of a material having a piezoelectric property (piezoelectric material) such as a piezoelectric ceramic represented by PZT (Pb(lead) zirconate titanate) or a polymeric piezoelectric element represented by PVDF (polyvinylidene difluoride). Further, in recent years, a piezoelectric material containing PZNT (oxide containing lead, zinc, niobium and titanium) monocrystal may be used, which is expected to contribute to improvements in sensitivity and band of ultrasonic transducer.

When a voltage is applied to the electrodes of such an ultrasonic transducer by sending pulse or continuous wave electric signals, the piezoelectric material expands and contracts. By the expansion and contraction, pulse or continuous ultrasonic waves are generated from the respective vibrators, and an ultrasonic beam is formed by combining those ultrasonic waves. Further, the respective vibrators expand and contract by receiving the propagating ultrasonic waves to generate electric signals. These electric signals (RF signals) are used as reception signals of ultrasonic waves.

The ultrasonic transmitting and receiving apparatus main body 2 includes plural switching circuits 21, plural transmitting circuits 22, plural receiving circuits 23, a computer 30, a storing unit 40 and a display unit 50.

The plural switching circuits 21 connect the plural ultrasonic transducers 10 incorporated in the ultrasonic probe 1 to the plural transmitting circuits 22 respectively at the time of ultrasonic wave transmission, and connect the ultrasonic transducers 10 incorporated in the ultrasonic probe 1 to the plural receiving circuits 23 respectively at the time of ultrasonic wave reception.

Each of the transmitting circuits 22 includes a D/A converter for converting waveform data supplied from a waveform data generating unit 31 into an analog drive signal and a class-A power amplifier for amplifying the drive signal outputted from the D/A converter. The D/A converter operates at a high speed with high resolving power and is compliant with a sampling frequency equal to or more than ten times the frequency of the transmission signal of ultrasonic wave (carrier frequency in the case where the transmission signal is modulated wave). Preferably, the D/A converter can output an analog signal having a frequency band equal to or more than 100 MHz. Further, the resolving power of the D/A converter is ten or more bits, and, preferably, 14 or more bits. Alternatively, in place of the class-A amplifier, a power amplifier of B-class, C-class or less, especially, a D-class or E-class power amplifier may be used.

Each receiving circuit 23 includes a preamplifier, a TGC (time gain compensation) amplifier and an A/D (analog/digital) converter. The RF signal outputted from each ultrasonic transducer 10 is amplified by the preamplifier and subjected to attenuation correction according to a distance to which the ultrasonic wave reaches within the object by the TGC amplifier.

The RF signal outputted from the TGC amplifier is converted into a digital signal by the A/D converter. As a sampling frequency of the A/D converter, at least about a tenfold frequency of the frequency of the ultrasonic wave is required, and a 16-fold or more frequency of the frequency of the ultrasonic wave is desirable. Further, as the resolving power of the A/D converter, resolving power of ten or more bits is desirable.

The computer 30 controls the transmission and reception of ultrasonic wave based on software (control program) stored in the storing unit 40. In the storing unit 40, a recording medium such as a hard disk, a flexible disk, an MO, an MT, a RAM, a CD-ROM or a DVD-ROM can be used. The waveform data generating unit 31, a scan control unit 32, filter banks 34A and 34B, waveform interpolation units 35A and 35B, delaying units 36A and 36B, addition units 37A and 37B and a display image computing unit 38 are realized as a function block by a central processing unit (CPU) and software included in the computer 30. Further, the computer 30 has a reception memory 33.

The waveform data generating unit 31 generates waveform data representing combined drive waveform formed by combining plural drive waveforms with respect to each ultrasonic transducer 10 and supplies one set of waveform data to the plural transmitting circuits 22, respectively, in order to simultaneously transmit plural kinds of ultrasonic beams having different spectra from the ultrasonic probe 1 in plural directions. These transmitting circuits 22 generate plural drive signals based on the one set of waveform data and supply them to the ultrasonic transducers 10, respectively.

Thereby, transmission focus processing is performed, and ultrasonic beams "A" and "B" are simultaneously transmitted from the ultrasonic probe 1 in plural directions as shown in FIG. 1. The scan control unit 32 sequentially sets the transmission directions of the ultrasonic beams "A" and "B" and varies these transmission directions of the ultrasonic beams in accordance with a predetermined scan method. Further, the scan control unit 32 sequentially sets reception directions of ultrasonic echoes at the time of reception.

Here, a transmission and reception method that characterizes the present invention will be described.

Figure 2:
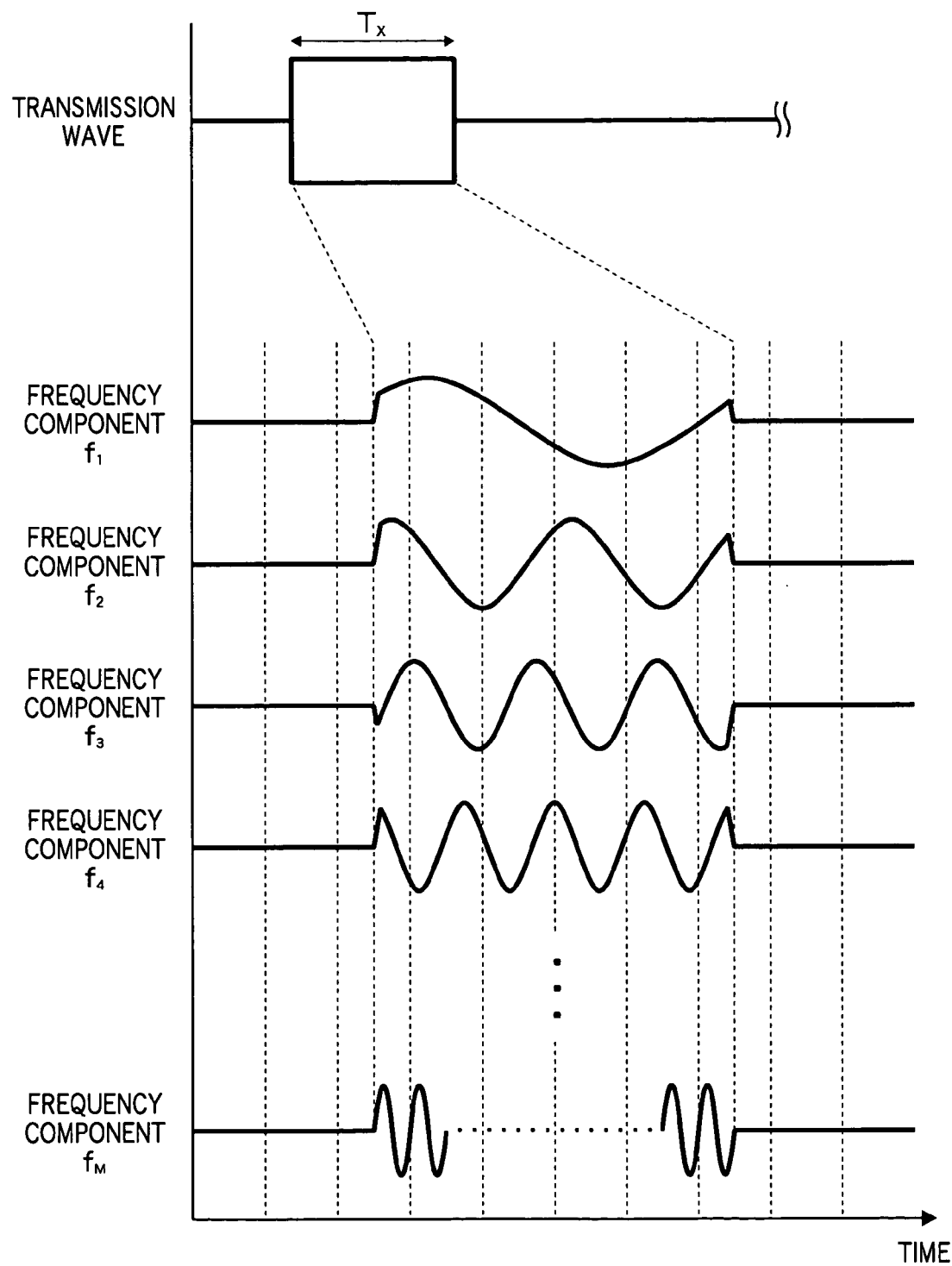
FIG. 2 is a diagram for explanation of generation of transmission wave in the one embodiment of the present invention.

FIG. 2 is a diagram for explanation of generation of transmission wave in the embodiment. In order to generate a continuous transmission waveform in transmission time period Tx as shown in FIG. 2, some frequency components are selected from among sub-band frequency components $f_1$ to $f_M$ orthogonal to each other and having different center frequencies from each other in the transmission band, and the selected frequency components are added to each other after phases thereof are shifted randomly so that pseudo white noise is generated. Here, with respect to integer numbers m=1, 2, ..., M, the center frequency of the frequency component $f_m$ is m/Tx. When correlation between the sub-band frequency components $f_1$ to $f_M$ and the frequency component $f_m$ are obtained and integrated in the duration Tx, integration values of the frequency components other than the frequency component $f_m$ as an auto-correlation become zero. Further, by thus shifting the phase randomly, in the focal position of transmission wave, it becomes possible to concentrate power spatially without concentrating power temporally. Thereby, the peak value of transmission wave can be suppressed smaller than that in the conventional transmission and reception method.

In the conventional transmission and reception method, the transmission time is on the order of 1 μsec per channel, and, when the beam is tilted in the sector scan, the transmission time is on the order of 15 μsec as a total of all channels. Contrary, in the embodiment, in order not to cause the power to concentrate temporally, the transmission time is set to on the order of 20 μsec per channel.

Figure 3:
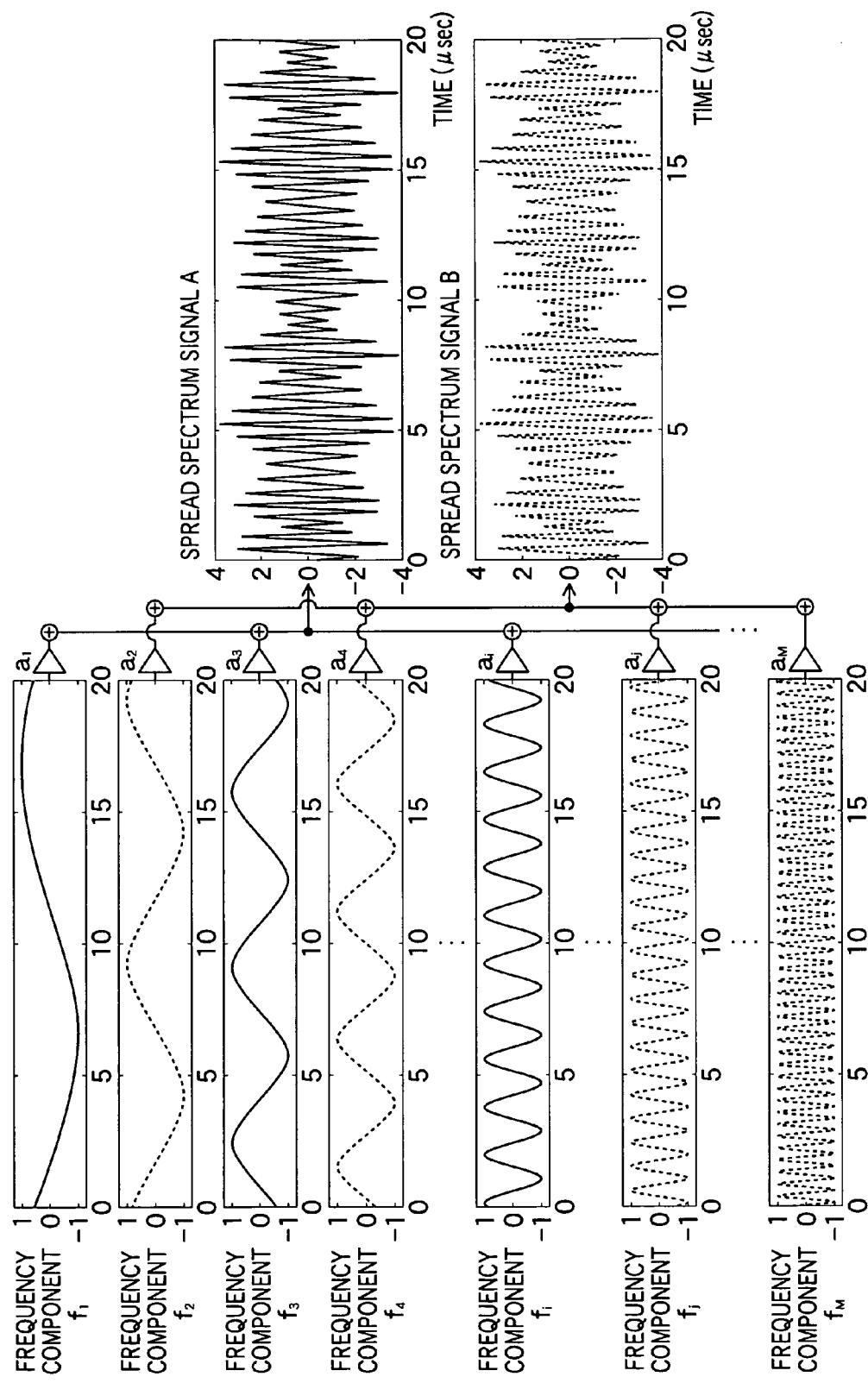
FIG. 3 is a diagram for explanation of generation of spread spectrum signals in the one embodiment of the present invention.

FIG. 3 is a diagram for explanation of generation of spread spectrum signals in the embodiment. As shown in FIG. 3, the phase relationship is randomly shifted by providing different delay amounts to the sub-band frequency components $f_1$ to $f_M$ and the frequency component $f_i$ discretely selected from among the frequency components $f_1$ to $f_M$ is multiplied by coefficient $a_i$ and added to each other (i=1, 3, ..., M−1), and thereby, spread spectrum signal "A" having a waveform that has been turned into pseudo white noise is obtained. Similarly, the frequency component $f_j$ discretely selected from among the frequency components $f_1$ to $f_M$ is multiplied by coefficient $a_j$ and added to each other (j=2, 4, ..., M), and thereby, spread spectrum signal "B" having a waveform that has been turned into pseudo white noise is obtained.

Furthermore, a first set of waveforms obtained by performing delay processing for transmission beam forming on the spread spectrum signal "A" and a second set of waveforms obtained by performing delay processing for transmission beam forming on the spread spectrum signal "B" are combined, and thereby, a set of drive signals to be supplied to ultrasonic transducers are obtained.

Figure 4:
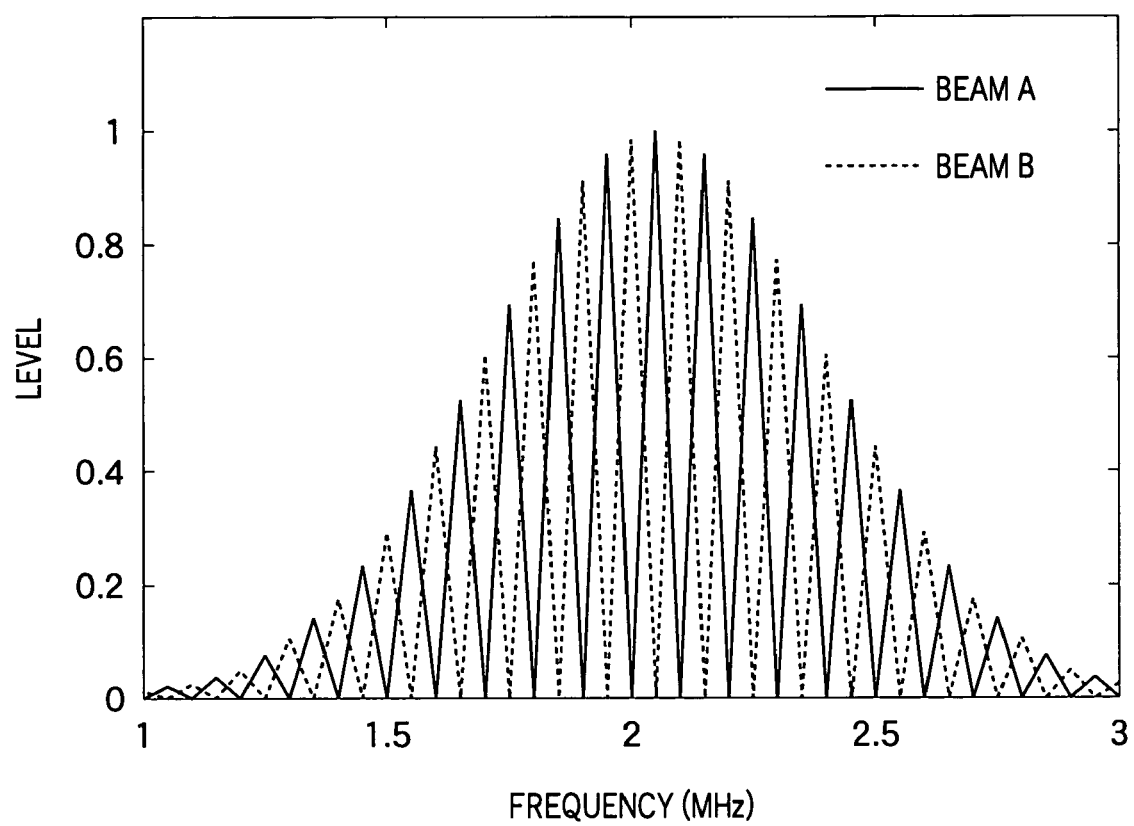
FIG. 4 shows an example of spectra of transmission waves in the one embodiment of the present invention.
Figure 5A:
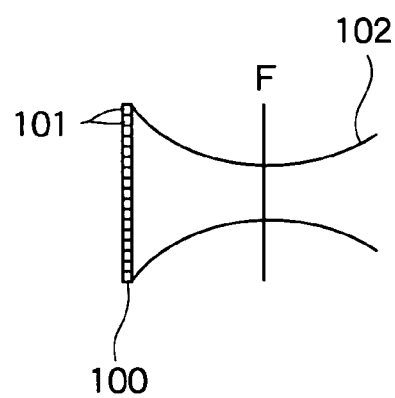
FIG. 5A is a schematic diagram for explanation of transmission of an ultrasonic beam according to a conventional method.
Figure 5B:
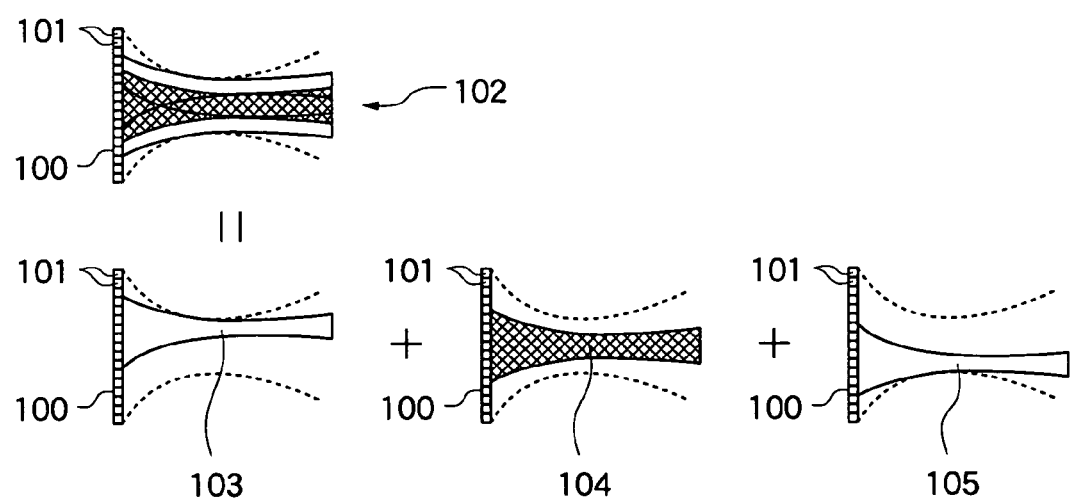
FIG. 5B is a schematic diagram for explanation of reception of a nultrasonic beam according to a conventional method.

FIG. 4 shows an example of spectra of transmission waves in the embodiment. By multiplying the spectra of the spread spectrum signals "A" and "B" by frequency characteristics of ultrasonic transducers, spectra of ultrasonic beams "A" and "B" are obtained. The spectrum of transmission wave is diffused in the form of a comb in the embodiment, while the spectrum of transmission wave concentrates in the conventional transmission and reception method.

In the case where plural ultrasonic beams are simultaneously transmitted in plural directions in accordance with the multi-beam method, crosstalk among ultrasonic beams can be reduced by providing plural kinds of spectra as shown in FIG. 4 to those ultrasonic beams, respectively.

Although the ultrasonic transmitting and receiving apparatus simultaneously transmits two kinds of ultrasonic beams in two directions in the embodiment, the ultrasonic transmitting and receiving apparatus according to the present invention may simultaneously transmit three or more kinds of ultrasonic beams in three or more directions. In either case, the waveform data generating unit 31 as shown in FIG. 1 generates plural kinds of spread spectrum signals by adding frequency components to each other at a predetermined rate. The frequency components have been discretely selected from among plural frequency components having different center frequencies from each other in a transmission band. Further, the waveform data generating unit 31 obtains one set of waveforms for ultrasonic transducers with respect to each transmission beam by performing delay processing for transmission beam forming on each spread spectrum signal, and generates waveform data representing one set of waveforms by combining plural sets of waveforms for forming plural transmission beams.

For example, in the case where three kinds of ultrasonic beams are transmitted, the waveform data generating unit 31 generates a first spread spectrum signal having frequency components $f_1$, $f_4$, $f_7$, ..., a second spread spectrum signal having frequency components $f_2, f_5, f_8, \ldots$, and a third spread spectrum signal having frequency components $f_3, f_6, f_9, \ldots$ Further, the waveform data generating unit 31 performs delaying processing for transmission beam forming on each spread spectrum signal to obtain three sets of transmission waveforms with respect to three transmission beams, combines them to generate waveform data representing one set of transmission waveforms, and supplies them to the plural transmitting circuits 22. The transmitting circuits 22 generate plural drive signals based on the one set of transmission waveforms and supplies them to the ultrasonic transducers 10, respectively. Those ultrasonic transducers 10 simultaneously transmit three kinds of ultrasonic beams corresponding to the first to third spread spectrum signals from the ultrasonic probe 1 in plural directions according to the plural drive signals.

Thus, the point where plural frequency components (sub-band or sub-carrier) are utilized is common to the transmission and reception method in the embodiment and OFDM (orthogonal frequency division multiplexing) used in a communication method, and plural kinds of spread spectrum signals can be generated by the same circuitry as that used in OFDM.

At the time of reception, an ultrasonic echo generated by the reflection of the transmitted ultrasonic beam "A" from the object includes the solid-line spectrum as shown in FIG. 4, and an ultrasonic echo generated by the reflection of the transmitted ultrasonic beam "B" from the object includes the broken-line spectrum as shown in FIG. 4. Thus, the received ultrasonic echoes lack the half of the information in the transmission band. Consequently, even when the spread spectrum signal obtained by combining parts of the sub-band frequency components $f_1$ to $f_M$ is compressed, it cannot be compressed into a desired monopulse due to comb-like lack of frequency components. Therefore, in the embodiment, a desired monopulse is obtained by filling the frequency components lacking in the comb-like form by interpolation and performing pulse compression processing thereon.

Referring to FIG. 1 again, the reception memory 33 stores digital signals outputted from the A/D converters of the plural receiving circuits 23 with respect to each ultrasonic transducer in chronological order. The filter bank 34A first performs phase matching processing on the digital signals read from the reception memory 33 so as to form reception focal points corresponding to the transmitted ultrasonic beam "A", and then, adds those to each other. Thereby, reception focus processing is performed and reception signals or sound ray signals, in which focal points of ultrasonic echoes are narrowed, are formed. Next, the filter bank 34A performs comb filter processing corresponding to the frequency components of the ultrasonic beam "A" on the reception signal, and extracts the frequency components $f_1, f_3, \ldots, f_{2n-1}, \ldots, f_{M-1}$ of the ultrasonic beam "A" from the reception signal. Thereby, the frequency components of the ultrasonic beam "B" can be reduced and the crosstalk can be improved. Further, the waveform interpolation unit 35A obtains the frequency components $f_1$ to $f_M$ by interpolating the frequency components lacking in the transmission band and outputs these frequency components.

Similarly, the filter bank 34B first performs phase matching processing on the digital signals read from the reception memory 33 so as to form reception focal points corresponding to the transmitted ultrasonic beam "B", and then, adds those to each other. Thereby, reception focus processing is performed and reception signals or sound ray signals, in which focal points of ultrasonic echoes are narrowed, are formed. Next, the filter bank 34B performs filter processing corresponding to the frequency components of the ultrasonic beam "B" on the reception signal, and extracts the frequency components $f_2, f_4, \ldots, f_{2n}, \ldots, f_M$ of the ultrasonic beam "B" from the reception signal. Thereby, the frequency components of the ultrasonic beam "A" can be reduced and the crosstalk can be improved. Further, the waveform interpolation unit 35B obtains the frequency components $f_1$ to $f_M$ by interpolating the frequency components lacking in the transmission band and outputs these frequency components.

In order to restore the phase relationship among plural frequency components that have been randomly shifted at the time of transmission, the delaying units 36A and 36B provide different delay amounts to the plural frequency components respectively outputted from the waveform interpolation units 35A and 35B to restore the phase relationship.

The addition units 37A and 37B add the plural frequency components respectively outputted from the delaying units 36A and 36B. Thereby, pulse compression is performed and reception signals having monopulse waveforms are formed.

The display image computing unit 38 generates image data based on the reception signals outputted from addition units 37A and 37B. For example, the display image computing unit 38 generates B-mode image data for displaying ultrasonic images on a two-dimensional screen based on reception signals obtained by sector scan, generates Doppler image data for displaying a target moving object such as a blood stream based on reception signals obtained according to the Doppler method, or generates color flow mapping (CFM) image data for displaying stable Doppler images based on reception signals obtained by CFM. Here, CFM refers to two-dimensional Doppler tomography by which the operation of scanning an object with an ultrasonic beam in the azimuth direction while repeating transmission of fixed ultrasonic beam until the Doppler frequency stable at some degree is obtained at each distance is repeated in a predetermined scan range.

Furthermore, the display image computing unit 38 converts image data in the sound ray space into the image data in the physical space by converting the scan format of the image data. The display unit 50 includes a display device such as a CRT or LCD for example, and displays ultrasonic images based on the image data generated by the display image computing unit 38.

In the embodiment, the waveform data generating unit 31, the scan control unit 32, the filter banks 34A and 34B, the waveform interpolation units 35A and 35B, the delaying units 36A and 36B, the addition units 37A and 37B and the display image computing unit 38 are formed by a CPU and software. However, they may be formed by a digital circuit or an analog circuit.

Further, instead of transferring real waveform data from the waveform data generating unit 31 to the respective transmitting circuits 22, oscillating circuits for each sub-band are incorporated in the respective transmitting circuits 22, the scan control unit 32 may supply the respective transmitting circuits 22 with control signals for controlling three kinds of amounts of amplitude, initial phase, delay amount as control amounts that dynamically vary.

The invention claimed is:

1. An ultrasonic transmitting and receiving apparatus comprising:
    an ultrasonic probe including ultrasonic transducers for transmitting ultrasonic waves to an object to be inspected according to plural drive signals and receiving ultrasonic echoes reflected from the object to output plural reception signals, respectively;
    drive signal generating means for generating plural drive signals for simultaneously transmitting plural ultrasonic beams from said ultrasonic probe in plural directions, said plural ultrasonic beams corresponding to plural spread spectrum signals having different sets of comb teeth obtained by adding frequency components, which have been discretely selected from among a predetermined number of frequency components having different center frequencies in a transmission band, to each other at a predetermined rate; and reception side signal processing means for performing signal processing on the plural reception signals respectively outputted from said plural ultrasonic transducers, performing phase matching and addition on the plural reception signals subjected to the signal processing so as to form plural reception focal points corresponding to a number of ultrasonic beams transmitted from said ultrasonic probe and thereby obtain sound ray signals, performing filter processing and interpolation processing on each of the sound ray signals to obtain said predetermined number of frequency components in which lacking information has been restored, and performing pulse compression processing by providing different delay amounts to said predetermined number of frequency components and adding said predetermined number of frequency components to each other at a predetermined rate.

2. An ultrasonic transmitting and receiving apparatus according to claim 1, wherein said drive signal generating means generates plural drive signals for simultaneously transmitting plural ultrasonic beams from said ultrasonic probe in plural directions, said plural ultrasonic beams corresponding to plural spread spectrum signals having different sets of comb teeth obtained by adding frequency components, which have been discretely selected from among a predetermined number of frequency components orthogonal to each other and having different center frequencies in a transmission band, to each other at a predetermined rate.

3. An ultrasonic transmitting and receiving apparatus according to claim 1, wherein said drive signal generating means generates plural drive signals for simultaneously transmitting plural ultrasonic beams from said ultrasonic probe in plural directions based on plural groups of frequency components selected in a predetermined order from among a predetermined number of frequency components having different center frequencies in a transmission band, said plural ultrasonic beams corresponding to plural spread spectrum signals having different sets of comb teeth obtained by adding frequency components within respective groups of frequency components to each other at a predetermined rate.

4. An ultrasonic transmitting and receiving apparatus according to claim 1, wherein said drive signal generating means generates the plural drive signals by combining plural waveforms obtained by performing delaying processing for transmission beam forming on the plural spread spectrum signals.

5. An ultrasonic transmitting and receiving apparatus according to claim 1, wherein said drive signal generating means includes:

waveform data generating means for respectively generating waveform data representing waveforms of plural drive signals for simultaneously transmitting the plural ultrasonic beams from said ultrasonic probe in plural directions; and plural transmitting circuits for generating the plural drive signals based on the waveform data generated by said waveform data generating means and supplying the plural drive signals to said ultrasonic probe.

6. An ultrasonic transmitting and receiving apparatus according to claim 5, further comprising:

scan control means for controlling said waveform data generating means so as to change directions of the plural ultrasonic beams transmitted from said ultrasonic probe in accordance with a predetermined scan method.

7. An ultrasonic transmitting and receiving apparatus according to claim 1, wherein said drive signal generating means obtains the plural spread spectrum signals turned into pseudo white noise by shifting phase relationships among a predetermined number of frequency components having different center frequencies from each other in a transmission band and adding frequency components, which have been discretely selected from among said predetermined number of frequency components, to each other at a predetermined rate.

8. An ultrasonic transmitting and receiving apparatus according to claim 1, wherein said reception side signal processing means forms plural reception focal points corresponding to a number of ultrasonic beams simultaneously transmitted from said ultrasonic probe.

* * * * *